United States Patent
Sanders et al.

(10) Patent No.: US 10,265,833 B2
(45) Date of Patent: Apr. 23, 2019

(54) PORTABLE CAVITATION PEENING METHOD AND APPARATUS

(71) Applicant: The Boeing Company, Chicago, IL (US)

(72) Inventors: Daniel Gordon Sanders, Cle Elum, WA (US); Amanda Jean Thoreson, Portland, OR (US); Hali The Diep, Renton, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 15/693,409

(22) Filed: Aug. 31, 2017

(65) Prior Publication Data

US 2019/0061104 A1 Feb. 28, 2019

(51) Int. Cl.
| | |
|---|---|
| B23P 17/00 | (2006.01) |
| B24C 1/10 | (2006.01) |
| C21D 10/00 | (2006.01) |
| C21D 7/06 | (2006.01) |
| B24C 5/04 | (2006.01) |
| B21D 26/02 | (2011.01) |
| B05B 15/62 | (2018.01) |

(Continued)

(52) U.S. Cl.
CPC ............. B24C 1/10 (2013.01); B05B 9/0406 (2013.01); B05B 13/0431 (2013.01); B05B 15/62 (2018.02); B21D 26/02 (2013.01); B24C 5/04 (2013.01); C21D 7/06 (2013.01); C21D 10/00 (2013.01); G01N 3/10 (2013.01)

(58) Field of Classification Search
CPC .......... C21D 7/06; C21D 10/00; B05B 15/62; B05B 9/0406; B05B 13/0431; B05B 15/061; B21D 26/02; B24C 1/10; B24C 5/04; G01N 3/10

USPC ............................................................ 72/53
See application file for complete search history.

(56) References Cited

U.S. PATENT DOCUMENTS

| | | | |
|---|---|---|---|
| 6,280,302 B1 * | 8/2001 | Hashish | B24C 5/04 451/102 |
| 6,425,276 B1 * | 7/2002 | Hirano | B24C 1/10 134/10 |

(Continued)

FOREIGN PATENT DOCUMENTS

| | | |
|---|---|---|
| DE | 60031257 T2 | 2/2007 |
| DE | 60030341 T2 | 8/2007 |

(Continued)

OTHER PUBLICATIONS

Englsih Abstract of JP 2011-245582.*

(Continued)

*Primary Examiner* — David B Jones
(74) *Attorney, Agent, or Firm* — Kolisch Hartwell, P.C.

(57) ABSTRACT

A method of cavitation peening may include coupling a moveable water source to a portable nozzle, through a flexible conduit. The method may include positioning the nozzle adjacent a treatment surface and discharging a first and second stream of fluid through a first and second channel of the nozzle, with the second channel concentrically positioned around the first channel. The first stream may have a first pressure, and the second stream may have a second pressure, the first pressure being greater than the second pressure and the two streams combining to generate a cloud of cavitation bubbles.

20 Claims, 7 Drawing Sheets

(51) Int. Cl.
*G01N 3/10* (2006.01)
*B05B 9/04* (2006.01)
*B05B 13/04* (2006.01)

(56) References Cited

U.S. PATENT DOCUMENTS

| | | | |
|---|---|---|---|
| 6,855,208 B1 | 2/2005 | Soyama | |
| 6,993,948 B2 | 2/2006 | Offer | |
| 9,050,642 B2 * | 6/2015 | Alberts | B21D 26/02 |
| 9,200,341 B1 | 12/2015 | Sanders et al. | |
| 9,739,695 B2 * | 8/2017 | Michishita | G01N 3/10 |

FOREIGN PATENT DOCUMENTS

| | | | | |
|---|---|---|---|---|
| EP | 1500712 B1 | | 8/2006 | |
| EP | 1170387 B1 | | 10/2006 | |
| JP | 4240972 B2 | | 3/2009 | |
| JP | 2011-245582 | * | 12/2011 | B23P 17/00 |
| JP | 5578318 B2 | | 8/2014 | |
| JP | 2016221650 A | | 12/2016 | |

OTHER PUBLICATIONS

Soyama, et al., Use of Cavitating Jet for Introducing Compressive Residual Stress, Article in Journal of Manufacturing Science and Engineering, vol. 22, Feb. 2000, 7 pages.

Turski, et al., Engineering the residual stress state and microstructure of stainless steel with mechanical surface treatments, Article for Springer-Verlag, May 11, 2010, 8 pages.

Sato, et al., Using Cavitation Peening to Improve the Fatigue Life of Titanium Alloy Ti-6A1-4V Manufactured by Electron Beam Melting, Article for Scientific Research Publishing, Apr. 20, 2016, 11 pages.

Marcon, Andrea, Water Cavitation Peening for Aerospace Materials—A Dissertation Presented to the Academic Faculty at the Georgia Institute of Technology, Jan. 2017, 211 pages.

U.S. Patent and Trademark Office, Office action regarding U.S. Appl. No. 15/693,417, dated May 30, 2018, 10 pages.

* cited by examiner

PORTABLE CAVITATION PEENING METHOD AND APPARATUS

CROSS-REFERENCES

The following U.S. patents are incorporated herein, in their entireties, for all purposes: U.S. Pat. Nos. 6,855,208 B1, and 9,200,341 B1.

FIELD

This disclosure relates to systems and methods for cavitation peening. More specifically, the disclosed examples relate to a movable apparatus for cavitation peening a stationary workpiece.

INTRODUCTION

Shot peening is well known as a method of enhancing fatigue strength, increasing resistance to Stress Corrosion Cracking (SCC), and inducing residual compressive stress in a material. For example, aircraft repair involves grinding components, which can build tensile stress. Peening of repaired components can relieve the tensile stress, and replace it with beneficial compressive stress. In shot peening, spherical shot is propelled at high speed and impacts the material's surface, causing plastic deformation.

However, shot peening results in surface roughening, and for certain shot media (e.g. cast shot) can stain the treated surface. Expendable shot can be expensive, and also poses a substantial safety risk for operators. Water cavitation peening has shown promise as an alternative process that cleans rather than staining, at a low cost and low operating risk.

Currently used cavitation peening systems generally require a workpiece to be submerged in a tank of water. The peening apparatus is permanently located where parts are manufactured, or where repaired parts are sent to be peened. An apparatus capable of on-site peening is desirable, to speed up repairs and allow parts to be peened in or near their routine location.

SUMMARY

A method of cavitation peening may include coupling a moveable water source to a portable nozzle, through a flexible conduit. The method may include positioning the nozzle adjacent a treatment surface and discharging a first and second stream of fluid through a first and second channel of the nozzle, with the second channel concentrically positioned around the first channel. The first stream may have a first pressure, and the second stream may have a second pressure, the first pressure being greater than the second pressure and the two streams combining to generate a cloud of cavitation bubbles.

The present disclosure provides systems, apparatuses, and methods relating to cavitation peening. In some examples, a cavitation peening system may include a portable nozzle assembly and a movable fluid source. In some examples, the nozzle assembly may include a co-flow nozzle configured to generate a cloud of cavitation bubbles. In some examples, a method of cavitation peening may include translating a cloud of cavitation bubbles across a stationary treatment area on a work piece at a substantially constant stand-off distance.

Features, functions, and advantages may be achieved independently in various examples of the present disclosure, or may be combined in yet other examples, further details of which can be seen with reference to the following description and drawings.

DESCRIPTION

Figure 1:
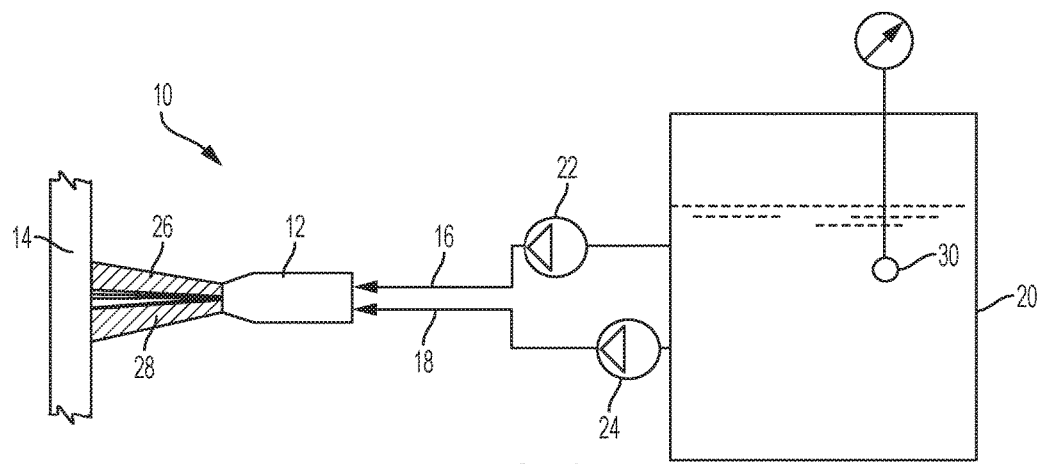
FIG. 1 is a schematic illustration of a portable cavitation peening system being used to peen an aircraft landing strut.

Various aspects and examples of a system for cavitation peening having a nozzle assembly and fluid source, as well as related methods, are described below and illustrated in the associated drawings. Unless otherwise specified, a system for cavitation peening and/or its various components may, but are not required to, contain at least one of the structure, components, functionality, and/or variations described, illustrated, and/or incorporated herein. Furthermore, unless specifically excluded, the process steps, structures, components, functionalities, and/or variations described, illustrated, and/or incorporated herein in connection with the present teachings may be included in other similar devices and methods, including being interchangeable between disclosed examples. The following description of various examples is merely illustrative in nature and is in no way intended to limit the disclosure, its application, or uses. Additionally, the advantages provided by the examples described below are illustrative in nature and not all examples provide the same advantages or the same degree of advantages.

Definitions

The following definitions apply herein, unless otherwise indicated.

"Substantially" means to be more-or-less conforming to the particular dimension, range, shape, concept, or other aspect modified by the term, such that a feature or component need not conform exactly. For example, a "substantially cylindrical" object means that the object resembles a cylinder, but may have one or more deviations from a true cylinder.

"Comprising," "including," and "having" (and conjugations thereof) are used interchangeably to mean including but not necessarily limited to, and are open-ended terms not intended to exclude additional, unrecited elements or method steps.

Terms such as "first", "second", and "third" are used to distinguish or identify various members of a group, or the like, and are not intended to show serial or numerical limitation.

"Coupled" means connected, either permanently or releasably, whether directly or indirectly through intervening components.

Overview

In general, a cavitation peening system may include a portable nozzle assembly connected by flexible conduits to a movable fluid supply. A method of using a cavitation peening system may include steps of positioning the nozzle assembly adjacent a treatment surface, and discharging a first fluid stream and a second fluid stream such that the streams combine to generate a cloud of cavitation bubbles.

Examples, Components, and Alternatives

The following sections describe selected aspects of exemplary portable cavitation peening systems, nozzle assemblies, and fluid sources, as well as related systems and/or methods. The examples in these sections are intended for illustration and should not be interpreted as limiting the entire scope of the present disclosure. Each section may include one or more distinct embodiments or examples, and/or contextual or related information, function, and/or structure.

A. First Illustrative System

FIG. 1 shows a schematic diagram of an exemplary portable cavitation peening system generally indicated at 10, including a nozzle assembly 12 directed at a treatment surface 14. Two flexible conduits 16, 18 supply pressurized fluid to the nozzle assembly. A tank 20 supplies fluid to two pumps, a first pump 22 connected to conduit 16 and a second pump 24 connected to conduit 18. First pump 22 pressurizes the fluid to a first pressure, and second pump 24 pressurizes the fluid to a second, lower, pressure.

Nozzle assembly 12 discharges a first stream 26 of fluid at the first pressure, and a second stream 28 at the second pressure. The two streams are discharged concentrically, such that the streams combine to generate a cloud of cavitation bubbles. An operator may maintain nozzle assembly 12 at a distance from treatment surface 14, and the distance may be approximately equal to twice a length of the cloud. Nozzle assembly 12 may be operated manually, or may be connected to an automated system.

A sensor cluster 30 is submerged in the fluid of tank 20 to monitor the fluid for relevant parameters. For example, the cluster may include sensors for temperature and oxygen content. The sensor data may be displayed by visual indicators on an exterior surface of the tank. The data may also be output to an electronic controller, or communicated to an operator by visual, auditory, or other means.

B. Second Illustrative System

Figure 2:
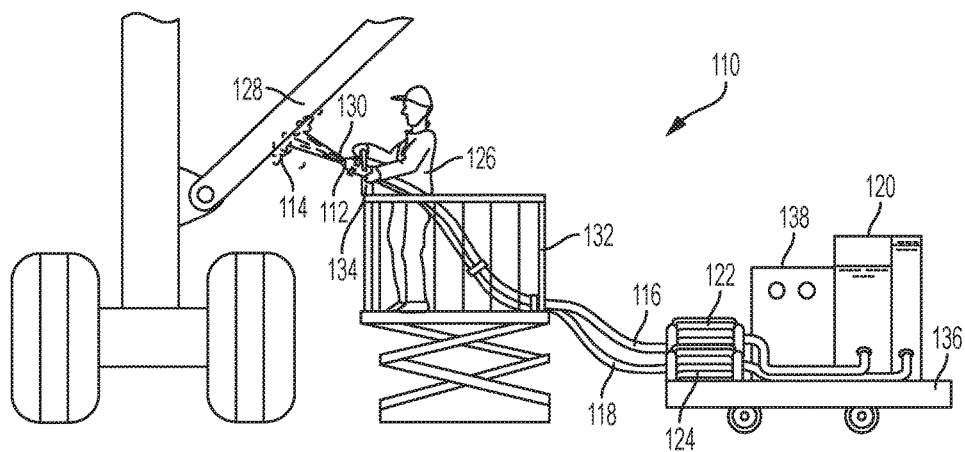
FIG. 2 is a schematic diagram of another portable cavitation peening system.

FIG. 2 is an illustration of a portable cavitation peening system 110 in use. An operator 126 directs a nozzle assembly 112 toward a strut 128 for stabilizing landing gear of an aircraft. The nozzle assembly generates a cloud of cavitation bubbles and discharges a flow of water 130 onto the strut. Strut 128 remains in place on the landing gear during peening, and operator 126 stands on a lift 132 to bring nozzle assembly 112 adjacent to a treatment area 114 on strut 128. Operator 126 directs nozzle assembly 112 toward treatment area 114 until the area has been sufficiently treated, and then may direct the nozzle toward a next treatment area. The operator may continue translating the nozzle assembly to new treatment areas until strut 128 has been fully treated.

Nozzle assembly 112 includes a handle grasped by operator 126, and a stand 134. The stand rests on a railing of lift 132 to allow operator 126 to direct nozzle assembly 112 without supporting the weight of the nozzle assembly. The stand may also assist operator 126 in maintaining a correct stand-off distance from strut 128 and a correct angle between flow of water 130 and treatment area 114.

A pair of hoses 116, 118 supply water to nozzle assembly 112 from pumps 122, 124. Pump 122 may pressurize the water to approximately between 1,000 and 5,000 pounds per square inch (PSI), preferably about 3000 PSI, or to any appropriate pressure. Pump 124 may pressurize the water to a lower pressure, for example, 50 PSI, or may leave the water at atmospheric pressure, or supply a laminar flow of water at any appropriate pressure.

Hoses 116, 118 connect separately to nozzle assembly 112, but are bundled for ease of movement by operator 126. The hoses may be tied at intervals, enclosed in a conduit, or otherwise arranged. Electrical, data, or other cables may also be bundled with hoses 116, 118 and connected to nozzle assembly 112.

Pumps 122, 124 pump water from a water reservoir tank 120. In the pictured example, tank 120 has two compartments with pump 122 drawing from a first compartment and pump 124 drawing from a second compartment. In some examples the first and second compartments may store water at different pressures or temperatures, or may hold different fluids.

Tank 120 and pumps 122, 124 are mounted on a wheeled platform 136 with a chiller unit 138. Tank 120 may be filled via chiller 138, which may cool and filter incoming water. Controlling temperature and impurity levels of incoming water may be desirable to provide optimal conditions at nozzle assembly 112 for cavitation cloud formation. A mechanism may be included in tank 120 to allow stored water to be cycled through chiller 138 when the water temperature rises past an acceptable operating temperature.

Chiller 138 or tank 120 may include a port or connector appropriate to connect with an airport water supply. The tank may have been filled at a water supply prior to being moved to the work area near to the aircraft landing gear, or the tank may continue to be filled during peening if a water supply is available at the work area. Tank 120 may be of a size to hold sufficient water for an effective treatment period. For example, if peening of treatment area 114 requires 20 minutes, and nozzle assembly 112 discharges water at a flow rate of 3 gallons per minute, then tank 120 may have a volume of at least 60 gallons.

Wheeled platform 136 may be an integrated component of cavitation peening system 110, or may be a means of transport provided at a work site. For example, at an airport, system 110 may be transported on a motorized vehicle. At a work area, tank 120, pumps 122, 124, and chiller 138 may remain on the vehicle during peening and be moved as needed by the vehicle for access to aircraft components. For such examples, tank 120, pumps 122, 124, and chiller 138 may be removably mounted in a chassis or frame to allow easy loading and unloading. In other examples, tank 20 may include casters on a bottom face and pumps 122, 124 may be secured to an upper face of the tank. Any effective, movable configuration may be used.

As shown in FIG. 2, pumps 122, 124 and chiller 138 are separately accessible. Such a configuration may allow easy in-field replacement of parts. For example, cavitation peening system 110 may be useful for repairs performed in remote areas, where harsh conditions may accelerate wear or where downtime for repairs is undesirable. If an interior component of pump 122 were to malfunction, another model or type of pump, with appropriate pressure and flow rate parameters, might be substituted while pump 122 undergoes repair.

In other examples, pumps 122, 124, and chiller 138 may be enclosed in a single unit with tank 120 for easy of transportation and handling. Controls for all components and display of data from any sensors may be available on an exterior of the single unit.

Cavitation peening system 110 may be used for peening, or may also be used for other applications. For example, the system may be used for cleaning surfaces or may be used for controlled deformation. With the introduction of an abrasive media into the cavitation cloud, the system may also be used for smoothing rough surfaces.

C. Third Illustrative System

Figure 3:
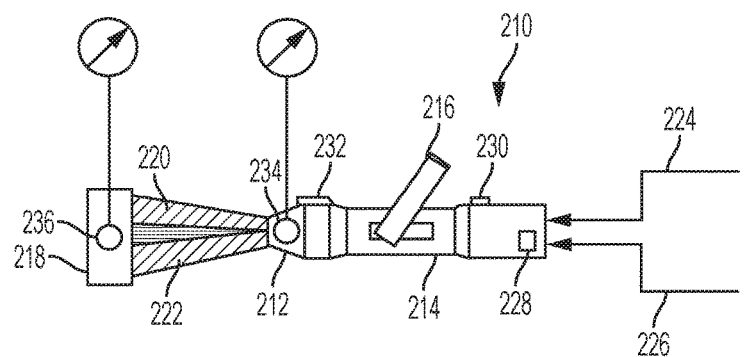
FIG. 3 is a schematic diagram of an exemplary nozzle assembly.

FIG. 3 shows a schematic diagram of a nozzle assembly 210, for cavitation peening. The assembly includes a co-flow nozzle 212, a body portion 214, and a handle 216. Nozzle 212 is directed toward a calibration puck 218, discharging an inner stream 220 and an outer stream 222 of fluid to generate a cloud of cavitation bubbles. Two flexible conduits supply fluid to nozzle assembly 210, a first conduit 224 with fluid at a first pressure for inner stream 220, and a second conduit 226 with fluid at a second pressure for outer stream 222.

Nozzle assembly 210 further includes controls 228, a gauge 230, and a guide device 232. Controls 228 stop or start flow of fluid from co-flow nozzle 212. The controls may affect inner stream 220 and outer stream 222 concurrently, or separate controls may be provided for each stream. Controls 228 may also include any other functions of nozzle assembly 210, or a cavitation peening system with which nozzle assembly 210 is used. For example, controls 228 may allow an operator to adjust temperature or pressure of inner stream 220 and/or outer stream 222. Controls 228 may be operatively connected to an electronic controller of the cavitation peening system.

One or more sensors 234 are mounted in co-flow nozzle 212 to measure properties of the fluid near the point of discharge. The sensors may be mounted such that they do not impede fluid flow, interfere with formation of a cavitation cloud by the co-flow nozzle, or otherwise reduce the efficacy of the co-flow nozzle. In some examples, some or all of sensors 234 may be disposed in body portion 214 of nozzle assembly 210. In some examples, sensors may be disposed on an exterior of the nozzle assembly.

Sensors 234 may measure properties of inner stream 220, outer stream 222, and/or an external environment. The measured properties may include, but are not limited to pressure, temperature, flow rate, dissolved oxygen, impurity levels, ambient noise, ultrasonic noise, or vibration. Measurement data from each sensor may be displayed on nozzle assembly 210, for example by gauge 230, or may be communicated to an electronic controller.

Calibration puck 218 may be used prior to peening of a workpiece. The puck includes one or more sensors 236 to measure impulsive pressures produced by nozzle assembly 210. The sensors may include load cells, piezoelectric transducers, pressure-sensitive films, or any effective sensors. Puck 218 may also include a material resistant to erosion by cavitation impacts to limit mass loss during calibration. In other examples, puck 218 may include replaceable inserts or test substrates with known material properties. An operator may perform an erosion test on an insert to measure cavitation intensity of nozzle assembly 210. Puck 218 may also include any permanent or replaceable testing components appropriate for testing cavitation or peening properties of fluid discharged from nozzle assembly 210.

An operator or controller may use measured impulsive pressure or cavitation intensity from the calibration puck and sensor data from nozzle assembly 210 to adjust fluid supplied by conduits 224, 226. By adjusting fluid parameters such as absolute pressure, pressure ratio, flow rate, temperature, or dissolved oxygen levels, peening performed with nozzle assembly 210 may be optimized to a desired intensity.

Figure 4:
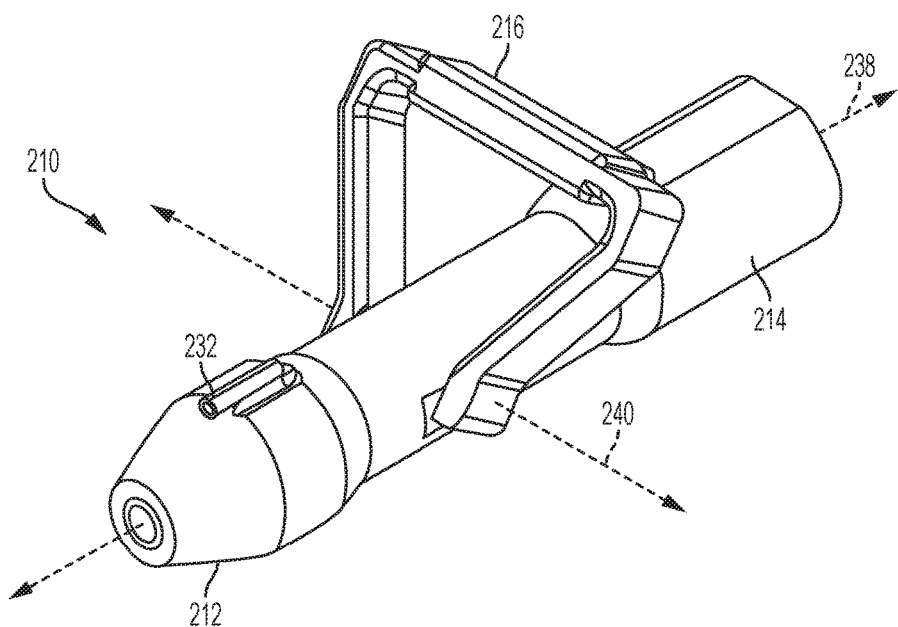
FIG. 4 is an isometric view of the nozzle assembly of FIG. 3.

FIG. 4 is an isometric view of nozzle assembly 210, showing an elongate axis 238 defined by body portion 214. Handle 216 is mounted on the body such that it pivots about a pivot axis 240 perpendicular to elongate axis 238. A manual operator may thereby orient nozzle assembly 210 at a desired angle with respect to a treatment surface, while maintaining a comfortable angle between the operator and handle 216. A wide range of motion of handle 216 may also be desirable to allow an operator to access treatment areas under, over, or around other components.

Handle 216 may also include features to aid effective or ergonomic grip, or prevent repetitive stress injury to an operator using nozzle assembly 210 for extended periods. For example, handle 216 may include a cam lever to selectively secure the handle at a desired pivot position, or handle 216 may include a rubber-like material that provides effective grip when wet. In some examples, handle 216 may include padding to absorb vibration transferred from the pressurized fluid or cavitation cloud.

In FIGS. 3-5A, nozzle assembly 210 is shown with a pivoting handle, but any effective handle may be used. In some examples handle 216 may be configured to connect to a robotic system such as a CNC arm. Examples suitable for manual operation may include handle 216 forming a pistol shape with body portion 214, or two handles mounted on opposite sides of body portion 214 and extending perpendicular to elongate axis 238. In some examples, body portion 214 may have a wand shape to allow an operator to remain farther from a treatment area. Body portion 214 may include telescoping components to allow an operator to select a length appropriate for a specific workpiece or work area. Body 214 may include joints or flexible components to facilitate use of the nozzle assembly in tight spaces or difficult to access areas. A connector configured to mate with a tripod or other stand may be included on body portion 214, or a clip for attaching to a toolbelt or strap. Other effective nozzle configurations may be known to those skilled in the art, and any configuration may be used for nozzle assembly 210.

Figure 5A:
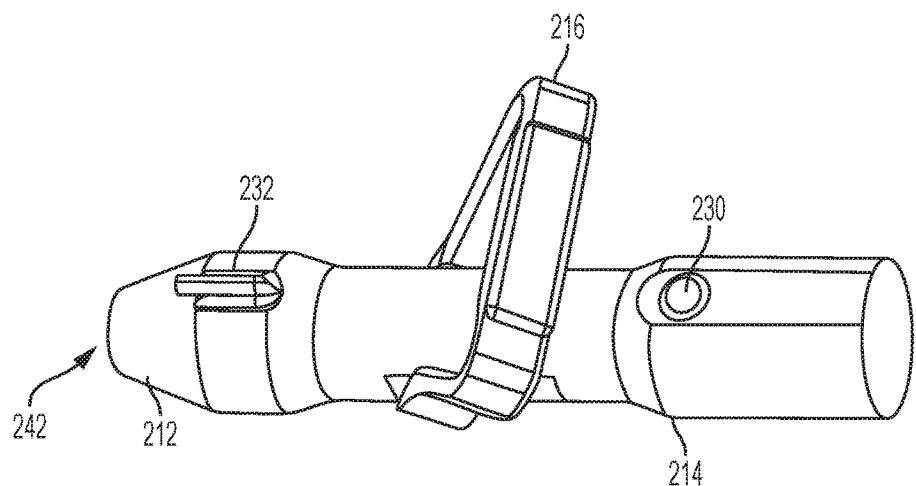
FIG. 5A is a top view of the nozzle assembly of FIG. 3.

FIG. 5A more clearly shows guide device 232 and gauge 230. Guide device 232 is a laser distance sensor configured to measure a stand-off distance between co-flow nozzle 212 and a treatment surface. The guide device may be calibrated to determine the distance from a tip 242 of co-flow nozzle 212 to a point of contact of the inner stream of fluid from the nozzle with the treatment surface. Gauge 230 displays the measured distance, and may include indicators providing information regarding a correct or desirable stand-off distance or range of distances.

Figure 5B:
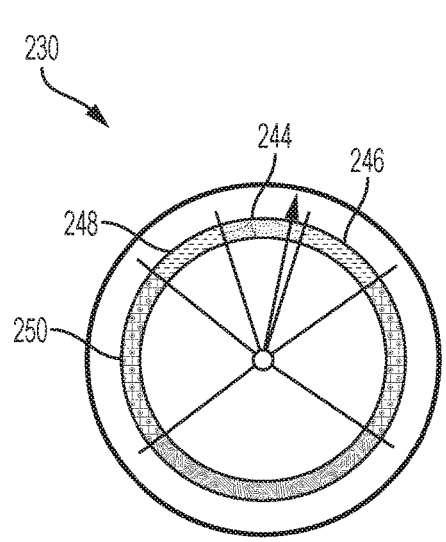
FIG. 5B is a schematic illustration of an exemplary stand-off distance indicator.
Figure 5C:
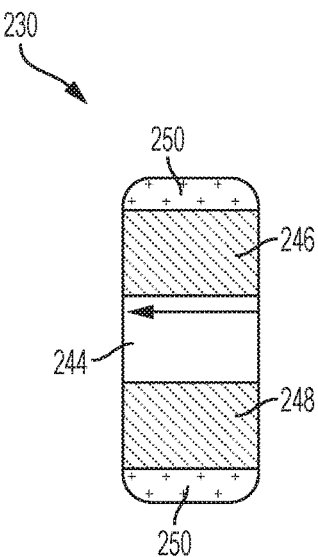
FIG. 5C is a schematic illustration of another stand-off distance indicator.

FIGS. 5B-C show two exemplary gauges. In FIG. 5B, a circular gauge is divided into 6 sections representing good 244 distance, buffers of acceptable but high 246 or low 248 distances, and unacceptable 250 distances. An indicator arrow shows current distance as measured by the guide device. The 6 sections may be labeled, and may be color coded. For example, good 244 may be green, buffers 246, 248 may be yellow, and unacceptable 250 may be red. FIG. 5C shows an alternative vertical gauge, with an indicator arrow, and 5 sections also including good 244, buffers 246, 248, and unacceptable 250. An operator may observe gauge 230 while positioning nozzle assembly 210, and adjust the nozzle closer to or farther from the treatment surface until the indicator arrow lies in good section 244.

In some examples, other means of measuring or indicating stand-off distance may be used. For example, one or more sets of LEDs may be mounted on co-flow nozzle 212 and oriented to shine parallel to a direction of fluid flow from the nozzle. Each set of LEDs may have red, yellow, and green settings, and be configured to change settings according to a measured stand-off distance. That is, the LEDs may shine a green pattern onto the treatment surface when co-flow nozzle 212 is at a stand-off distance in an optimal range, may shine a yellow pattern from the nozzle is at a distance in an acceptable range, and may shine a red pattern when the nozzle is at a distance outside the acceptable range.

In addition to stand-off gauge 230, nozzle assembly 210 may include gauges or indicators for any parameters of the nozzle or a cavitation peening system relevant to the operator. For example, the assembly may include a display screen for an electronic controller, an indicator of fluid levels in a fluid source, a temperature gauge, or a pressure gauge.

Nozzle assembly 210 may be made of a metal such as aluminum or titanium, may be composed of any suitable material, or may include multiple materials. Some or all of the nozzle assembly may be covered by a protective coating such as plastic, rubber or silicone. A protective coating may include shock-absorbent materials, and may be disposed at or be thicker at edges, corners, or vulnerable areas of nozzle assembly 210. In some examples, the nozzle assembly or a protective coating may include thermally insulating material. Any material, cover, or coating suitable to protect the assembly from weather conditions, splash-back of discharged fluid, or intrusion of dust and grit may be used. In some examples, nozzle assembly 210 may be configured to operate in harsh field conditions and withstand repeated impacts and exposure to muddy, dusty, or dirty environments.

Figure 6:
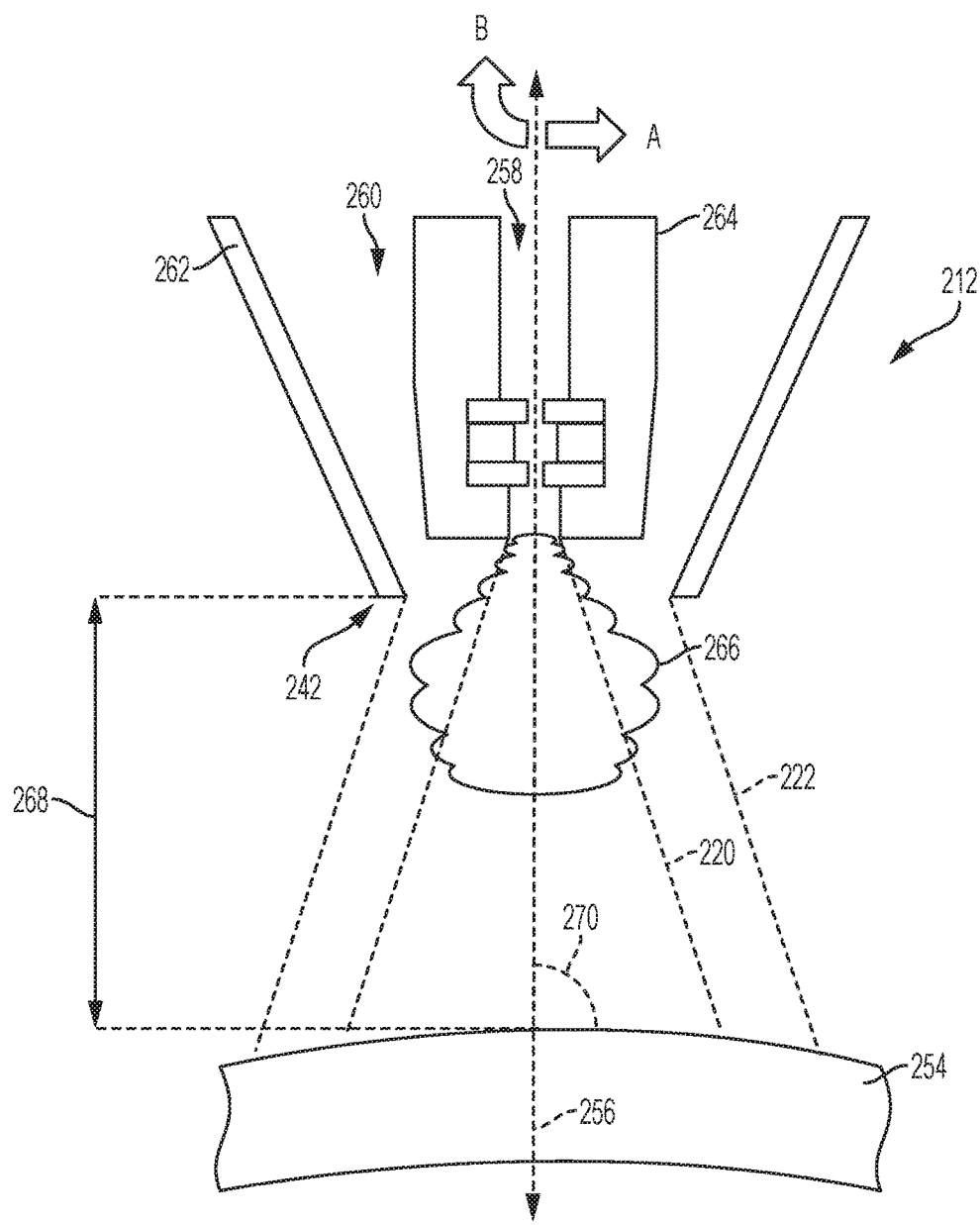
FIG. 6 is a schematic diagram of the nozzle assembly of FIG. 3.

FIG. 6 is a schematic diagram of co-flow nozzle 212 discharging fluid at a stationary treatment surface 254 in a treatment direction 256. The nozzle includes an inner channel 258 for inner stream 220 and an outer channel 260 for outer stream 222 that leads to tip 242 of the nozzle.

Outer walls 262 of co-flow nozzle 212 define outer channel 260, and surround inner channel 258. Outer walls 262 may be angled in as shown, may be parallel, or may be angled out. Inner channel 258 is defined by an inner nozzle 264 which is shown with a cavitator, spacer, and nozzle plate. Inner nozzle 264 may also have any effective geometry. For example, the nozzle may be cylindrical or conical.

Flexible conduits 224, 226 shown in FIG. 3 supply fluid to co-flow nozzle 212 via nozzle assembly 210. Conduit 226 is connected to inner channel 258 and supplies fluid at a first pressure, while conduit 224 is connected to outer channel 260 and supplies fluid at a second pressure. Conduits 224, 226 may be configured to channel separate fluid streams to the inner and outer channels. The first pressure is higher than the second pressure, and may be at least 1,000 PSI higher, may be at least 2,000 PSI higher, or may be any effective pressure.

Co-flow nozzle 212 may discharge outer stream 222 concentrically around inner stream 220, and may discharge the streams coaxially along treatment direction 256. The nozzle may mix the streams of fluid to generate a cloud 266 of cavitation bubbles.

Co-flow nozzle 212 is positioned at a stand-off distance 268 from treatment surface 254, and treatment direction 256 forms an angle 270 with the surface. Cavitation intensity experienced by treatment surface 254 may depend on the stand-off distance, and therefore it may be desirable to maintain a substantially constant stand-off distance within a given tolerance. For example, stand-off distance 268 may be kept within six to ten inches. It should be noted that in the pictured example cavitation cloud 266 extends only about halfway to treatment surface 254, as cavitation impact may be more effective beyond the cavitation cloud itself. Cavitation intensity may also be maintained by keeping cavitation cloud 266 within a range of three to five inches from the treatment surface.

An operator may translate co-flow nozzle 212 or the nozzle assembly over treatment surface 254 as indicated by arrow A. As shown in FIG. 6, treatment surface 254 is curved, and not planar. Accordingly, as nozzle 212 is translated, the operator may also rotate the nozzle as indicated by arrow B. The operator may thereby maintain angle 270. The angle may be maintained at approximately 90 degrees or within a range of 60 to 120 degrees.

Treatment surface 254 may also be planar, irregular, or have a complex structure. Nozzle 212 may be manipulated by the operator to follow a contour of surface 254. That is, the nozzle may be moved in three dimensions and rotated by the operator to accommodate curvatures in treatment surface 254.

A z-axis may be defined perpendicular to treatment surface 254 at a point where treatment direction 256 meets the surface. An x-y plane may also be defined tangent to the treatment surface at this point, and perpendicular to the z-axis. In the example shown in FIG. 6, treatment direction 256 coincides with the z-axis and arrow A is parallel to the x-y plane.

Nozzle 212 may be translated along surface 254 parallel to arrow A, or in any direction parallel to the x-y plane. To keep stand-off distance constant, nozzle 212 may also be translated up and down along the z-axis. Nozzle 212 may be rotated in the plane indicated by arrow B or any plane containing the z-axis. Nozzle 212 may be moved horizontally, vertically, or rotated in any manner necessary to achieve a correct distance and orientation relative to treatment surface 254.

Nozzle 212 may be manipulated manually, or by an automated system. In some examples, an operator grasping the handle of the nozzle assembly may estimate the correct translation and rotation by eye, to accommodate a curvature. In other examples, a robotic system may be programmed to perform the correct translation and rotation of the nozzle. Information regarding the structure of a workpiece may be entered into an automated system, such that the system may translate nozzle 212 over all surfaces of the workpiece while maintaining treatment direction 256 perpendicular to the surface and a substantially constant stand-off distance.

In some examples, abrasive media may be introduced into cavitation cloud 266. For example, wide-angle nozzle may be positioned at an edge of the cloud and disperse abrasive media to be energized by the cloud. In such examples, treatment surface 254 may be smoothed as well as peened and cleaned.

D. Fourth Illustrative System

Figure 7:
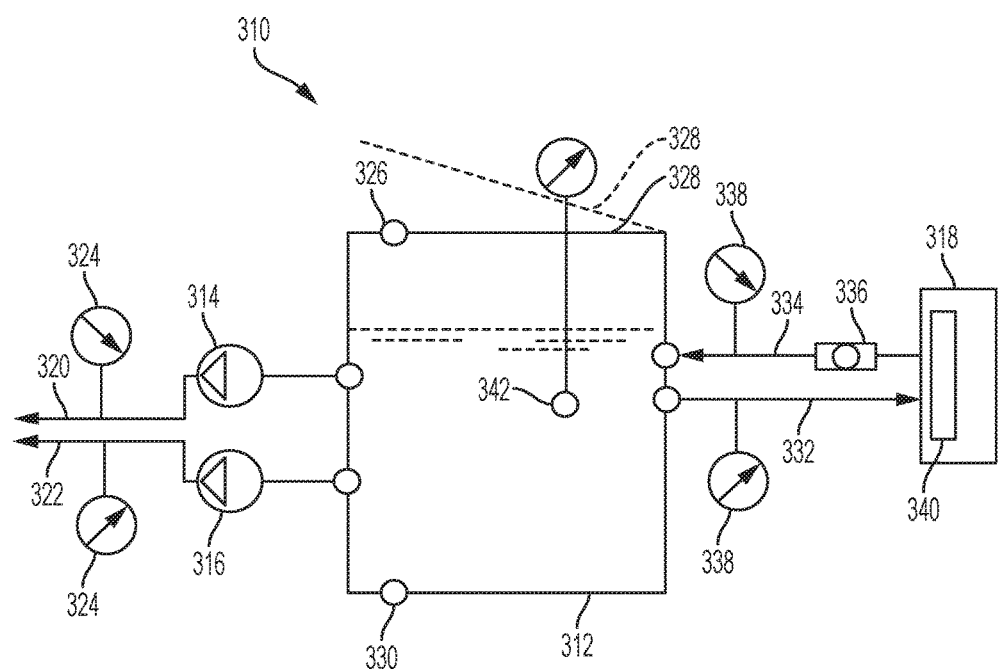
FIG. 7 is a schematic diagram of an exemplary source assembly.

FIG. 7 is a schematic diagram of a fluid source, generally indicated at 310, for use in a portable cavitation peening system. In the present example, fluid source 310 supplies water. In other examples, any fluid or fluids appropriate for cavitation peening may be supplied. Fluid source 310 may be configured for transportation. For example, the source may be mounted on a wheeled platform, or in a housing with carry-handles.

As shown in FIG. 7, a tank 312 is connected to two pumps 314, 316 and a temperature control unit 318. First pump 314 supplies water at a first pressure along a flexible conduit 320, and second pump 316 supplies water at a second pressure along a flexible conduit 322. Pumps 314, 316 may be the same or different, and may be any type of pump. In some examples tank 312 may be maintained at the second pressure, and flexible conduit 322 may supply water directly from the tank. In some examples, a booster pump may be connected to flexible conduit 320 in addition to first pump 314, in order to achieve a desired first pressure.

Flexible conduits 320, 322 may be any hosing or piping suitable for the first and second pressure. The conduits may include a thermal covering to maintain an optimal fluid temperature from tank 312 through to an attached nozzle assembly. As shown in FIG. 7, a sensor 324 is connected to each conduit. The sensor may measure pressure, temperature, or any relevant parameter of the water in the conduit. In some examples, one or both of conduits 320, 322 may include a flow control valve, or a pressure control valve.

Tank 312 includes a plurality of access points for input and output of water, which may include ports, valves, taps, drains, lids, or any effective mechanism. In the example pictured in FIG. 4, tank 312 has 7 access points, but any number of access points may be included. An input valve 326 is included at a top portion of tank 312, which may be compatible with a commonly used connection standard. For example, input valve 326 may be compatible with water supply hoses used in airports.

Tank 312 also includes a lid 328. The lid may allow access to an interior of tank 312 for cleaning, or maintenance of components of fluid source 310 that are mounted inside the tank. Lid 328 may also allow tank 312 to be filled from any available water supply or hose. Tank 312 includes a drain 330. The drain may be compatible with a connection standard, to allow draining of excess water for use by other equipment, or for other purposes. Drain 330 may also allow for tank 312 to be rapidly emptied when peening work is completed. Draining tank 312 may lighten source 310, and allow for easier transportation.

Input valve 326, lid 328, and drain 330 may all be tightly sealable. That is, when not in use, any access point on tank 312 may be sealed sufficiently to prevent leakage due to movement and forces resulting from transportation of the tank. Tank 312 may be sealed for transportation while connected to pumps 314, 316 and temperature control unit 318, or may be sealed to be transported separately.

Tank 312 may have any useful capacity. For example, when used with a portable cavitation peening system that discharges fluid at a rate of 2 gallons per minute and is intended for peening of parts requiring an average of 1 hour of peening, tank 312 may have a capacity of 150 gallons. Alternatively, tank 312 may have a capacity of 75 gallons, and a user may refill the tank halfway through the work. Preferably tank 312 may have a capacity such that when the tank is full, the tank may be reasonably moved by one or two workers either by lifting onto a motor vehicle, by dolly, or on attached wheels.

Tank 312 may be composed of plastic, fiberglass, stainless steel, or any durable material. Preferably, tank 312 may be composed of a material or materials appropriate to limit the weight of the tank and facilitate easy transportation. Tank 312 may be cylindrical, may be ridged to provide improved structural integrity for a thin material, or may be any effective shape.

Temperature control unit 318 may be connected to tank 312 via an input conduit 332 and an output conduit 334. A sight glass 336 is disposed on output conduit 334, to allow a user visual confirmation of water flow. In other examples, such a sight glass may be included in flexible conduit 320 or 322, or at any useful point in fluid supply 310. A temperature sensor 338 is connected to each conduit 332, 334. The sensor may also measure any relevant parameter of the water in the conduit. In some examples, one or both of conduits 332, 334 may include a flow control valve, or a pressure control valve.

Water may be drawn from tank 312 by a pump integrated into unit 318, by a pump connected to input conduit 332, may be fed by gravity, or may be moved by any effective mechanism. Water may be similarly, or differently returned to tank 312 from unit 318. Temperature control unit 318 may include a heating element, a cooling element, or both. In some examples, temperature control unit 318 may comprise a heating and/or cooling element mounted in tank 312.

Temperature control unit 318 includes a filter 340, which may filter minerals, debris, or contaminants from water cycled through the unit. Filtering impurities from water stored in tank 312 may facilitate effective peening, and reduce wear on components of a portable cavitation peening system. Filtering may also allow safe use of water from sources with unknown quality. In some examples, filter 340 may be integrated with input valve 326 of tank 312 or may be otherwise mounted in tank 312 to filter input water.

A sensor cluster 342 is mounted in tank 312, to monitor stored water. The cluster may include sensors for temperature, oxygen level, contaminants, or any relevant parameter. Data from sensor cluster 342, sensors 324, and sensor 338 may be displayed by visual indicators on an exterior surface of tank 312 or a housing of fluid source 310. The data may also be output to a controller module, or communicated to an operator by visual, auditory, or other means.

In some examples, fluid source 310 may also include a source of abrasive media. A hopper or other container may be mounted on tank 312, and may be connected to a nozzle assembly of a portable cavitation peening assembly by a flexible conduit. The abrasive media conduit may be bundled with conduits 320, 322.

E. Fifth Illustrative System

Figure 8:
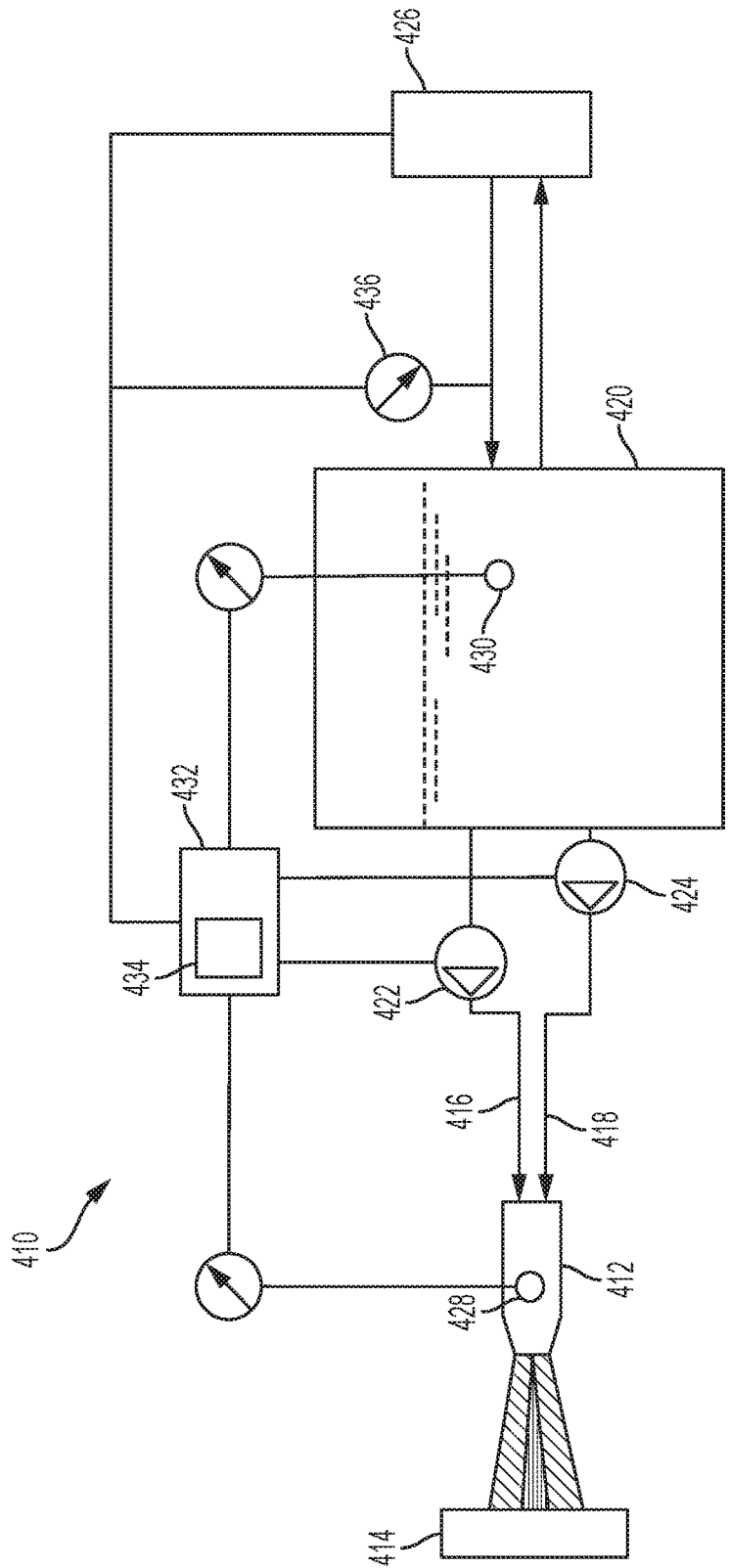
FIG. 8 is a schematic diagram of another portable cavitation peening system.

FIG. 8 is a schematic diagram of a portable cavitation peening system generally indicated at 410. The system includes a nozzle assembly 412, and a fluid source with a fluid tank 420, and two pumps 422, 424. The fluid source is connected to nozzle assembly 412 by flexible conduits 416, 418, and tank 420 is connected to a temperature control unit 426. A sensor cluster 428 is mounted in nozzle assembly 412, and another cluster 430 is mounted in tank 420.

Portable cavitation peening system 410 also includes an electronic controller 432, in wired or wireless communication with the rest of the system. The controller includes a processor and memory, and a control screen 434. The memory may include programmed instructions to be executed by the processor. Any type of controller may be used, and in some examples the controller may be analog, without processor or memory.

Controller 432 receives real-time sensor data from sensors of clusters 428, 430 and a temperature sensor 436. Data may include fluid temperature, fluid pressure, fluid oxygen content, fluid source level, ambient temperature, vibration, ultrasonic noise, or any useful parameters. In some examples, sensor data may be communicated at regular intervals or at a request by the controller. A laser guide device may communicate measurements to controller 432 of a stand-off distance from nozzle assembly 412 to a treatment area 414. Sensors of any type may also be mounted at any point in system 410 appropriate for collecting data. In some examples, additional sensors may be placed proximate a treatment area, on a workpiece.

Control screen 434 may display received sensor data. In some examples, controller 432 may perform mathematical or statistical analysis of collected data, and may display results of the analysis on control screen 434. For example, control screen 434 may display temperature and pressure measured in nozzle assembly 412, and stand-off distance to treatment 414. The control screen may further display a calculated cavitation intensity estimate, based on the measured temperature, pressure, and stand-off distance.

The controller memory may include acceptable operating ranges for the cavitation peening system. For example, an acceptable operating fluid source level may be between 20 and 150 gallons. Control screen 434 may display the acceptable operating ranges, or may dynamically display warnings when received sensor data is outside an acceptable operating range. For example, a fluid level indicator may be shown as red when fluid level is measured at 19 gallons. Controller 432 may also use audible alerts or alarms, lights or indicators mounted on nozzle assembly 412, or any other effective means to communicate warnings to an operator of system 410. Control screen 434 may also be configured to allow an operator to input acceptable operating ranges. An operator may specify acceptable levels for measured quantities, or for calculated quantities.

Controller 432 is operatively connected to pumps 422, 424, and temperature control unit 426. The controller is configured to activate and deactivate the pumps, adjust pressure, cycle water through the temperature control unit, and activate or deactivate heating or cooling elements of the unit. Nozzle assembly 412 may include controls for system 410, which may communicate with controller 432. Controller 432 may also be integrated with any systems of portable cavitation peening system 410, to send or receive data, activate or deactivate controls, or perform any appropriate function. In some examples, controller 432 may actuate delivery of abrasive media to the nozzle assembly.

Controller 432 may be configured to maintain parameters of portable cavitation peening system 410 within an acceptable operating range. For example, when fluid temperature is measured as higher than acceptable, the controller may activate a cooling element of temperature control unit 426 and cycle water of tank 420 through the unit. For another example, when pressure of an inner stream of nozzle assembly 412 is measured as lower than acceptable, the controller may adjust a pressure setting on pump 422. Controller 432 may also be configured to maintain a calculated quantity at an optimal level. For example, a user may input an optimal cavitation intensity to control screen 434, and controller 432 may adjust parameters of the system as required to maintain the input intensity.

In some examples, controller 432 may be configured to determine an optimal level for a measured or calculated quantity based on treatment surface properties. An operator may input characteristics of a workpiece to be treated to control screen 434, or may select a workpiece from a database of workpieces and associated characteristics stored in the controller's memory. Subsequently, throughout treatment of the workpiece, controller 432 may alter fluid discharge parameters as required to maintain the determined optimal level or levels.

F. Illustrative Method

Figure 9:
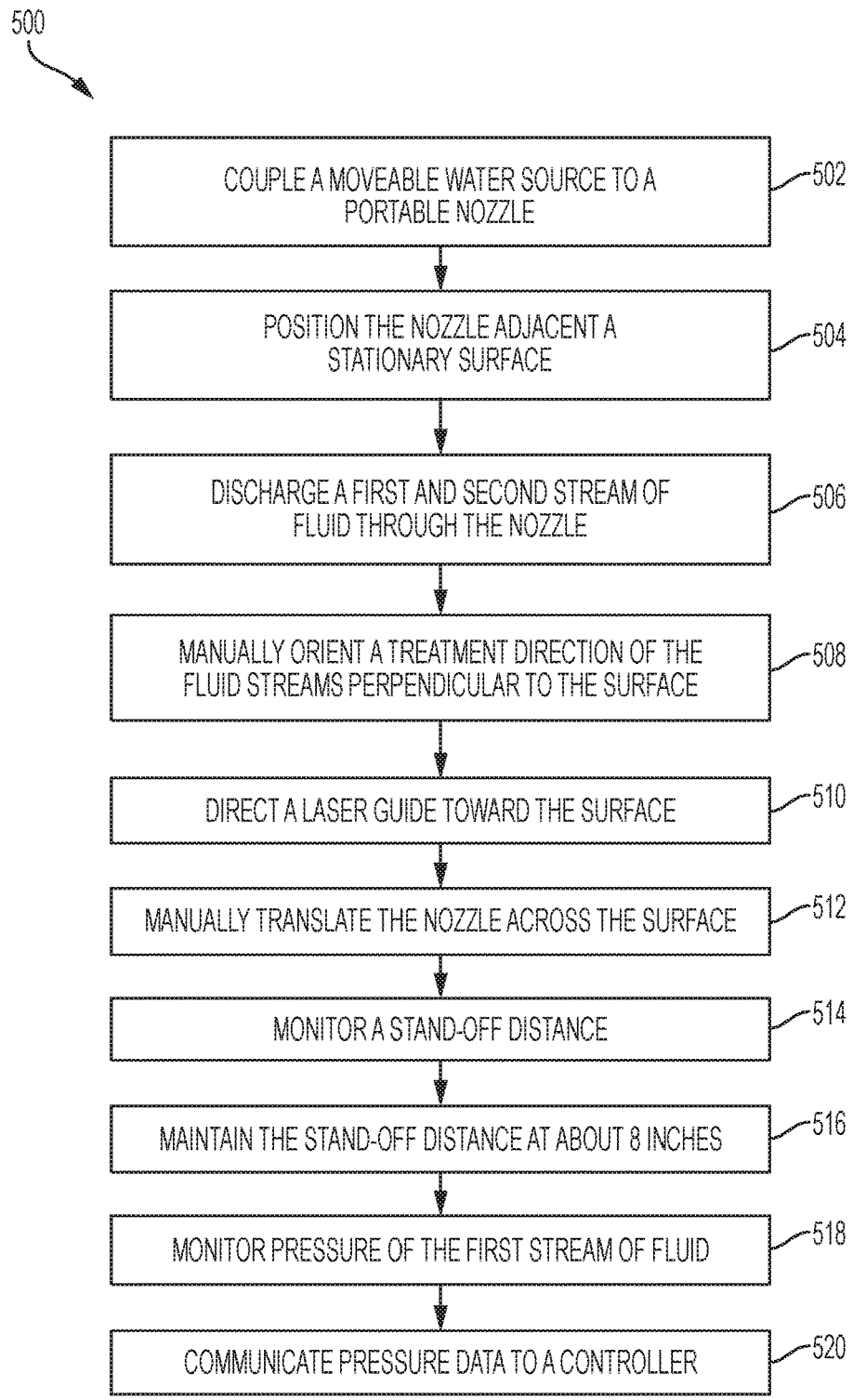
FIG. 9 is a flowchart illustrating a method of cavitation peening.

This section describes steps of an illustrative method for cavitation peening; see FIG. 9. Aspects of portable cavitation peening systems, nozzle assemblies, and fluid sources may be utilized in the method steps described below. Where appropriate, reference may be made to components and systems that may be used in carrying out each step. These references are for illustration, and are not intended to limit the possible ways of carrying out any particular step of the method.

FIG. 9 is a flowchart illustrating steps performed in an illustrative method, and may not recite the complete process or all steps of the method. Although various steps of method 500 are described below and depicted in FIG. 9, the steps need not necessarily all be performed, and in some cases may be performed simultaneously or in a different order than the order shown.

At step 502, the method includes connecting a moveable water source to a portable nozzle. The water source may include a tank and two pumps, while the nozzle may be a co-flow nozzle at a distal end of a nozzle body. The nozzle may be connected to the water source by a pair of flexible conduits. Together, the water source, nozzle, and conduits may form a portable cavitation peening system, which may further include other components such as an electronic controller and a temperature control unit. The nozzle may be connected to the water source prior to transportation to a work site, or may be connected at the work site prior to beginning treatment.

Step 504 of the method includes positioning the nozzle adjacent a stationary surface. The nozzle body may include a handle, and an operator may use the handle to bring the nozzle adjacent the surface. The operator may also position the moveable water source near the surface, such that the nozzle may reach all areas of the surface in need of treatment. To this end, the water source may include wheels or be placed on a wheeled cart. The pair of flexible conduits may be of sufficient length to allow the nozzle to reach treatment areas while the moveable water source is positioned at an appropriate distance.

For example, to treat a strut of an aircraft's landing gear, the operator may position the water source on the tarmac next to a lift. The operator may stand on the lift, and hold the nozzle by the handle up to the strut. The flexible conduits may extend from the water source, up to the lift, and to the nozzle. The system may also include features to facilitate the positioning process, such as bundled flexible conduits or a brake on the water source wheels.

At step 506, the method includes discharging a first and second stream of fluid through the nozzle. The co-flow nozzle may include a first channel and a second channel, the first channel being connected to a first of the pair of flexible conduits and the second channel being connected to the second of the pair of flexible conduits.

A first pump of the water source may supply water at a first pressure, and the second pump may supply water at a second pressure such that the first fluid stream is discharged at the first pressure and the second fluid stream is discharged at the second pressure. The first pressure may be higher than the second pressure.

The co-flow nozzle may be configured such that the first fluid stream is discharged concentrically with second fluid stream. That is, the first fluid stream may be surrounded by the second fluid stream. The two streams may be discharged coaxially along a treatment direction, and mix or combine to generate a cloud of cavitation bubbles.

The operator may initiate the streams of fluid by use of controls mounted on the nozzle body. The inner stream and outer stream may be activated by a single control, or may be separately initiated. The controls may be in direct communication with the pumps to begin movement of fluid, or the controls may be connected to an electronic controller that may perform a start-up sequence including multiple steps.

Before continuing treatment, the operator may evaluate conditions of the discharged fluid, the water source, or other components of the system. The water source, conduits, and nozzle may each include sensors monitoring fluid in the system. The nozzle may further include sensors to measure ambient conditions, or effects induced by cavitation such as vibration or ultrasonic noise. The operator may access data from the sensors by viewing a control screen of an electronic controller, or by viewing indicators directly connected to the sensors.

A treatment process may require a specific cavitation intensity or range of intensities. Factors such as fluid pressure, temperature, or dissolved gases may influence the cavitation intensity achieved by the portable cavitation peening system. To optimize cavitation intensity, the operator may evaluate data from sensors and adjust conditions of the fluid by activating a temperature control unit, cycling the fluid through a filter, adjusting a pump, or other changes to the system. In some examples, the operator may input a desired intensity into an electronic controller which may be configured to receive sensor data and adjust fluid conditions.

In some examples, the operator may evaluate the effective cavitation intensity or impact pressure of the portable cavitation unit by use of a calibration puck. The puck, made of a material resistant to erosion by cavitation impact, may include one or more sensors to report impacts experienced by the puck. The operator may direct the fluid discharged by the nozzle at the puck, and use the collected data to calibrate the cavitation cloud of the cavitation peening system to a desired intensity.

Step 508 includes manually orienting the treatment direction of the fluid streams perpendicular to the surface. The operator may use the handle of the nozzle to rotate or angle the nozzle so that the fluid contacts the surface at about 90 degrees, or in a range of 60 to 120 degrees. The operator may estimate the angle by eye, or may use a measurement device to calculate the angle.

At step 510, the method includes directing a laser guide toward the surface. The laser guide may be mounted on the nozzle, and directing the nozzle toward the surface may also effectively direct the laser guide. The guide may be configured to calculate a distance from a tip of the nozzle to the surface. This stand-off distance may be reported by a gauge on the nozzle body or may be communicated to an electronic controller.

The operator may adjust the nozzle position, bringing the nozzle tip closer to the surface or backing it away until the stand-off distance is within an acceptable range. The operator may use color-coded guides of a gauge on the nozzle body to find the correct stand-off distance, may be trained as to a correct stand-off distance, or may receive visual or auditory guidance from an electronic controller.

In some examples, an operator may adjust the nozzle to a correct stand-off distance prior to discharging fluid from the nozzle. In some examples, the operator may initiate the outer, second stream of lower pressure fluid and perform steps 508 and 510 before initiating the inner, first stream of high pressure fluid to generate a cloud of cavitation bubbles. Correctly positioning the nozzle before generating the cloud of cavitation bubbles may allow a more precise calculation of treatment time required for a starting area of the surface.

Step 512 includes manually translating the nozzle across the surface. The operator may position the nozzle adjacent a first treatment area, then translate the nozzle to a next treatment area. In some examples, the operator may scan the nozzle over the surface area at a constant rate. In other examples, the operator may hold the nozzle stationary at a first area, move the nozzle adjacent a second area, and hold the nozzle stationary once more. Any effective pattern or timing of treatment may be used.

Step 514 includes monitoring the stand-off distance, and step 516 includes maintaining the stand-off distance at about 8 inches. As the operator translates the nozzle over the surface, the laser guide may remain directed to the treatment surface and may continue to measure the stand-off distance. The operator may monitor the distance reported by the guide, and hold the nozzle at a substantially constant stand-off distance.

It should be noted that the distance may be constant within tolerance. That is, if the operator unintentionally varies the stand-off distance and then adjusts the nozzle back to the correct distance, provided the variation is within a predetermined tolerance, the operator may proceed with treatment without further corrective action.

At step 518, the method includes monitoring pressure of the first stream of fluid. A sensor may be mounted in the first channel of the nozzle to measure the fluid pressure. Step 520 includes communicating the pressure data to a controller. The controller may be configured to adjust the fluid pressure at the fluid source. That is, the controller may be operatively connected to the first pump, and may adjust the pump as needed to maintain a correct pressure of the first fluid.

The operator may also monitor the angle of the treatment direction of the fluid streams with the surface, and maintain the treatment direction perpendicular to the surface. The operator may further monitor other sensor data and adjust fluid conditions as needed to ensure that the cavitation peening system operates at an optimal intensity through treatment.

In some examples, the electronic controller may monitor the sensor data. In such examples, the controller may be programmed with acceptable fluid parameters. When measured conditions vary beyond acceptable levels, the controller may adjust the fluid parameters, may alert the operator, or both. For example, the electronic controller may monitor temperature of the discharged fluid. When the fluid temperature rises above an acceptable level, the controller may activate a chiller unit in the water source and may produce an alert sound audible to the operator.

In some examples, the operator may use controls of the nozzle to activate delivery of an abrasive media. The nozzle may inject the abrasive media into the discharged streams of fluid, proximate an edge of the cloud of cavitation bubbles. The operator may add abrasive media during peening treatment, or may use the cavitation peening system with abrasive media to perform surface smoothing or further cleaning once the peening treatment is completed.

G. Additional Examples and Illustrative Combinations

This section describes additional aspects and features of portable cavitation peening systems and methods, presented without limitation as a series of paragraphs, some or all of which may be alphanumerically designated for clarity and efficiency. Each of these paragraphs can be combined with one or more other paragraphs, and/or with disclosure from elsewhere in this application, including the materials incorporated by reference in the Cross-References, in any suitable manner. Some of the paragraphs below expressly refer to and further limit other paragraphs, providing without limitation examples of some of the suitable combinations.

A. A method of cavitation peening, comprising:
coupling a moveable fluid source to a portable nozzle through a flexible conduit, the nozzle having a first channel and a second channel,
positioning the nozzle adjacent a treatment surface of a work piece,
discharging toward the treatment surface, a first fluid stream through the first channel, and a second fluid stream through the second channel, the second channel being concentrically positioned around the first channel, wherein the first fluid stream has a first fluid pressure and the second fluid stream has a second fluid pressure, the first fluid pressure being greater than the second fluid pressure, wherein the first and second fluid streams combine to generate a cloud of cavitation bubbles.

A1. The method of A, further comprising:
translating the nozzle across the treatment surface at a constant stand-off distance.

A2. The method of A1, further comprising:
translating the nozzle along a Z-axis perpendicular to the treatment surface.

A3. The method of A, further comprising:
rotating the nozzle to accommodate a curvature in the treatment surface.

A4. The method of A, wherein the positioning step is performed manually.

A5. The method of A, wherein the positioning step is performed robotically.

A6. The method of A, wherein the nozzle directs the first and second fluid streams in a treatment direction toward the treatment surface.

A7. The method of A6, wherein the positioning step includes manually orienting the treatment direction of the fluid streams to form an angle with the treatment surface in the range of 60 degrees to 120 degrees.

A8. The method of A, wherein the nozzle has a tip portion, the positioning step including maintaining the tip of the nozzle at a stand-off distance from the treatment surface in the range of six inches to ten inches.

A9. The method of A, wherein the positioning step includes maintaining the cloud of cavitation bubbles a distance from the treatment surface in the range of three inches to five inches.

A10. The method of A, wherein the nozzle has a laser guide device, the positioning step including directing the laser guide device toward the treatment surface and determining a stand-off distance between a tip of the nozzle and the treatment surface.

A11. The method of A, wherein the discharging step includes monitoring the first fluid pressure of the first fluid stream passing through the nozzle.

A12. The method of A11, further comprising:
communicating pressure data sensed in the nozzle to a controller, the controller being programmed to adjust fluid pressure at the fluid source.

A13. The method of A11, wherein the monitoring step includes displaying the first fluid pressure on a gauge connected to the nozzle.

A14. The method of A, further comprising:
monitoring the temperature of fluid passing through the nozzle.

A15. The method of A14, further comprising:
communicating fluid temperature data sensed in the nozzle to a controller, the controller being programmed to adjust fluid pressure at the fluid source.

B. An apparatus for cavitation peening, comprising:
a fluid source,
a first pump device configured to receive a first fluid stream from the fluid source,
a second pump device configured to receive a second fluid stream from the fluid source,
a nozzle assembly configured to be translated over a stationary treatment area on a work piece, each of the pumps being connected to the nozzle via a flexible conduit, the nozzle being configured to mix fluid received from the first and second pumps to generate a cloud of cavitation bubbles.

B1. The apparatus of B, wherein the nozzle assembly includes a handle configured for manual manipulation of the nozzle.

B2. The apparatus of B, wherein the first pump device pumps the first fluid stream at a first pressure, and the second pump device pumps the second fluid stream at a second pressure, the first pressure being higher than the second pressure.

B3. The apparatus of B2, wherein the first pressure is at least 1000 p.s.i. greater than the second pressure.

B4. The apparatus of B2, wherein the first pressure is at least 2000 p.s.i. greater than the second pressure.

B5. The apparatus of B, wherein the nozzle assembly is configured to discharge fluid from the second fluid stream concentrically around fluid from the first fluid stream.

B6. The apparatus of B, wherein the flexible conduits carrying the first and second fluid streams are at least partially bundled together.

B7. The apparatus of B, wherein the nozzle assembly has a tip and a laser guide configured to detect a stand-off distance between the tip and a treatment surface of a work piece.

B8. The apparatus of B, wherein the nozzle assembly has a gauge indicating the stand-off distance.

B9. The apparatus of B, wherein the nozzle assembly has a gauge indicating a pressure level of the first fluid stream.

B10. The apparatus of B, wherein the nozzle assembly includes a body portion having an elongate axis.

B11. The apparatus of B10, wherein the handle forms a pistol shape with the body portion.

B12. The apparatus of B10, wherein the handle is pivotable around an axis perpendicular to the elongate axis.

B13. The apparatus of B10, wherein the handle includes two graspable projections extending laterally from opposite sides of the body portion.

C. A fluid delivery system for cavitation peening, comprising:
a co-flow nozzle assembly configured to generate a cloud of cavitation bubbles in a fluid stream, and to be manually translated across a stationary treatment area on a work piece, and
a portable fluid source connected to the nozzle assembly via first and second flexible conduits.

C1. The fluid delivery system of C, wherein the fluid source includes a first pump connected to the first flexible conduit, and a second pump connected to the second flexible conduit, the nozzle assembly having an inner channel and an outer channel, the first pump being configured to deliver fluid to the inner channel at a first fluid pressure, and the second pump being configured to deliver fluid to the outer channel at a second fluid pressure, the first fluid pressure being higher than the second fluid pressure.

D. A method of treating a work piece, comprising:

manually translating a cloud of cavitation bubbles across a stationary treatment area on a work piece at a substantially constant stand-off distance D1. The method of D, further comprising:

discharging a first fluid stream and a second fluid stream through a portable nozzle assembly.

D2. The method of D1, wherein the first fluid stream is discharged at a higher pressure than the second fluid stream.

D3. The method of D2, further comprising:

monitoring the temperature and pressure of the first fluid stream.

E. A dispensing system for cavitation peening, comprising:

a portable nozzle assembly including:

a body portion having an elongate axis, a first channel, and a second channel leading to a distal tip portion, a handle portion connected to the body portion, the handle portion being configured to direct the elongate axis of the body portion toward a stationary treatment area on a work piece, and to be translated over the treatment area at a constant stand-off distance.

E1. The dispensing system of E, wherein the second channel surrounds the first channel in the tip portion, the channels being configured to generate a cloud of cavitation bubbles for peening the treatment area.

E2. The dispensing system of E, wherein the handle is configured for manual manipulation by a human operator.

E3. The dispensing system of E2, wherein the handle forms a pistol shape with the body portion.

E4. The dispensing system of E2, wherein the handle portion is pivotable around an axis perpendicular to the elongate axis.

E5. The dispensing system of E2, wherein the handle portion includes two graspable projections extending laterally from opposite sides of the body portion.

E6. The dispensing system of E, further comprising:

a robotic system configured for coupling to the handle portion of the nozzle assembly, and programmed for manipulating the body portion to be directed toward the stationary treatment area on the work piece, and to be translated over the treatment area at a constant stand-off distance.

E7. The dispensing system of E, wherein the nozzle assembly has a laser guide connected to the body portion, configured to detect a stand-off distance between the tip portion and the treatment surface.

E8. The dispensing system of E, wherein the nozzle assembly has a gauge indicating the stand-off distance.

E9. The dispensing system of E, wherein the nozzle assembly has a gauge indicating a pressure level of the first fluid stream.

E10. The dispensing system of E, further comprising:

a puck configured for calibrating a cavitation cloud discharged from the nozzle assembly prior to treating the treatment area.

E11. The dispensing system of E10, further comprising:

a first flexible conduit connected to the first channel, and a second flexible conduit connected to the second channel, the conduits being configured for channeling separate fluid streams to the first and second channels.

F. A portable fluid supply apparatus, comprising a base configured for transport, a fluid reservoir supported by the base, a temperature control device for maintaining a desired temperature of fluid contained in the reservoir, a first pump device configured to receive fluid from the reservoir and to pump the fluid into a first flexible conduit at a first fluid pressure, and a second pump device configured to receive fluid from the reservoir and pump the fluid into a second flexible conduit at a second fluid pressure, the first fluid pressure being higher than the second fluid pressure such that a cavitation bubble cloud will be generated through a co-flow nozzle assembly connected to distal ends of the first and second flexible conduits, and a controller programmed to maintain desired temperature and pressure of fluid carried by the flexible conduits.

F1. The apparatus of F, wherein the base is equipped with wheels for moving the apparatus between locations.

F2. The apparatus of F, wherein the controller receives temperature data sensed in the nozzle assembly.

F3. The apparatus of F, wherein the controller receives pressure data sensed in the nozzle assembly.

F4. The apparatus of F, wherein the controller is programmed to alter a fluid discharge parameter at least partially based on identification of a characteristic of the work piece being treated.

Advantages, Features, Benefits

The different embodiments and examples of the systems and methods of portable cavitation peening described herein provide several advantages over known solutions for peening. For example, illustrative embodiments and examples described herein allow a workpiece to be peened and cleaned in a single process.

Additionally, and among other benefits, illustrative embodiments and examples described herein allow components to be peened on-site and in place.

Additionally, and among other benefits, illustrative embodiments and examples described herein reduce expendables costs and improve operator safety.

No known system or device can perform these functions, particularly in field conditions. Thus, the illustrative embodiments and examples described herein are particularly useful for peening of repairs. However, not all embodiments and examples described herein provide the same advantages or the same degree of advantage.

CONCLUSION

The disclosure set forth above may encompass multiple distinct examples with independent utility. Although each of these has been disclosed in its preferred form(s), the specific embodiments thereof as disclosed and illustrated herein are not to be considered in a limiting sense, because numerous variations are possible. To the extent that section headings are used within this disclosure, such headings are for organizational purposes only. The subject matter of the disclosure includes all novel and nonobvious combinations and subcombinations of the various elements, features, functions, and/or properties disclosed herein. The following claims particularly point out certain combinations and subcombinations regarded as novel and nonobvious. Other combinations and subcombinations of features, functions, elements, and/or properties may be claimed in applications claiming priority from this or a related application. Such claims, whether broader, narrower, equal, or different in scope to the original claims, also are regarded as included within the subject matter of the present disclosure.

What is claimed is:

1. A method of cavitation peening, comprising:
coupling a moveable fluid source to a portable nozzle through a flexible conduit, the nozzle having a first channel and a second channel,
positioning the nozzle adjacent a treatment surface of a work piece,
discharging toward the treatment surface, a first fluid stream through the first channel, and a second fluid stream through the second channel, the second channel being concentrically positioned around the first channel, wherein the first fluid stream has a first fluid pressure and the second fluid stream has a second fluid pressure, the first fluid pressure being greater than the second fluid pressure, wherein the first and second fluid streams combine to generate a cloud of cavitation bubbles;
translating the nozzle along a Z-axis perpendicular to the treatment surface until the cloud of cavitation bubbles is spaced from the treatment surface by a selected distance.

2. The method of claim 1, further comprising:
translating the nozzle across the treatment surface at a constant stand-off distance.

3. The method of claim 1, further comprising:
rotating the nozzle to accommodate a curvature in the treatment surface.

4. The method of claim 1, wherein the positioning step is performed manually.

5. The method of claim 1, wherein the positioning step is performed robotically.

6. The method of claim 1, wherein the nozzle directs the first and second fluid streams in a treatment direction toward the treatment surface.

7. The method of claim 6, wherein the positioning step includes manually orienting the treatment direction of the fluid streams to form an angle with the treatment surface in the range of 60 degrees to 120 degrees.

8. The method of claim 1, wherein the nozzle has a tip portion, the positioning step including maintaining the tip of the nozzle at a stand-off distance from the treatment surface in the range of six inches to ten inches.

9. The method of claim 1, wherein the positioning step includes maintaining the cloud of cavitation bubbles a distance from the treatment surface in the range of three inches to five inches.

10. The method of claim 1, wherein the nozzle has a laser guide device, the positioning step including directing the laser guide device toward the treatment surface and determining a stand-off distance between a tip of the nozzle and the treatment surface.

11. The method of claim 1, wherein the discharging step includes monitoring the first fluid pressure of the first fluid stream passing through the nozzle.

12. The method of claim 11, further comprising:
communicating pressure data sensed in the nozzle to a controller, the controller being programmed to adjust fluid pressure at the fluid source.

13. The method of claim 11, wherein the monitoring step includes displaying the first fluid pressure on a gauge connected to the nozzle.

14. The method of claim 1, further comprising:
monitoring the temperature of fluid passing through the nozzle.

15. The method of claim 14, further comprising:
communicating fluid temperature data sensed in the nozzle to a controller, the controller being programmed to adjust fluid pressure at the fluid source.

16. A method of treating a work piece, comprising:
transporting a cavitation peening apparatus to a work site, the cavitation peening apparatus including a portable co-flow nozzle assembly configured to generate a cloud of cavitation bubbles and a moveable fluid source, the portable co-flow nozzle coupled to the moveable fluid source through a flexible conduit; and
manually translating the cloud of cavitation bubbles across a stationary treatment area on a work piece at the work site, at a substantially constant stand-off distance.

17. The method of claim 16, further comprising:
discharging a first fluid stream and a second fluid stream through the portable co-flow nozzle assembly.

18. The method of claim 17, wherein the first fluid stream is discharged at a higher pressure than the second fluid stream.

19. The method of claim 18, further comprising:
monitoring the temperature and pressure of the first fluid stream.

20. The method of claim 1, wherein the selected distance is selected such that the cavitation cloud extends approximately halfway from the nozzle to the treatment surface.

* * * * *